May 22, 1962 M. E. GILL Plant Pat. 2,148
TANGELO TREE
Filed March 28, 1960
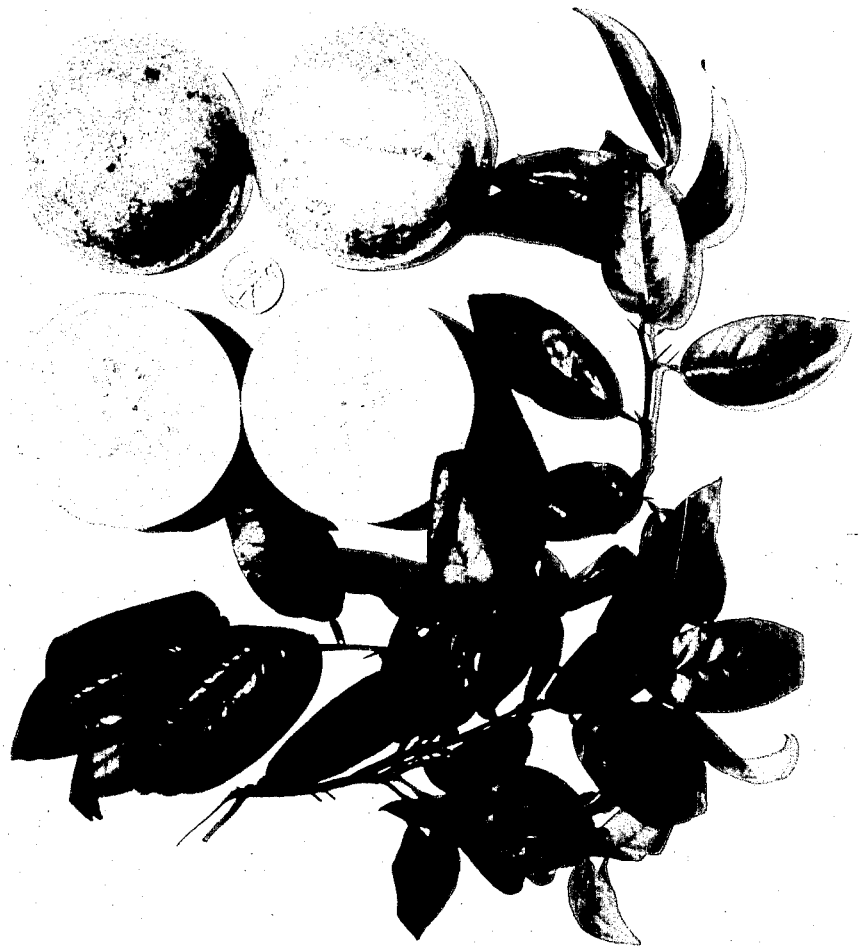

United States Patent Office

Plant Pat. 2,148
Patented May 22, 1962

2,148
TANGELO TREE

Marion Ellwood Gill, Winter Haven, Fla., assignor to Philip's Pride Incorporated, Winter Haven, Fla., a corporation of Florida Filed Mar. 28, 1960, Ser. No. 18,207
1 Claim. (Cl. 47—62)

This invention relates to a new variety of tangelo tree, the novel characteristics of which reside particularly in the excellent sectionizing qualities and distinctive color and flavor of the fruit.

Several years ago, I hybridized the King orange (unpatented) with the pollen of the Duncan seeded grapefruit (unpatented), and after a long and tedious process of selection, I transplanted a particular seedling of this cross to my property in Polk County, Florida, where it grew into a tree. When this tree matured wood for suitable budding stock, budwood was cut off, and the new variety was successfully asexually reproduced by the method of shield budding on Rough lemon (unpatented) root stock.

It is a marked characteristic of this new variety that the rind of the fruit has an external orangeish yellow color and its size approximates that of the Duncan grapefruit, while the flesh of the fruit is deep orange. The fruit combines the excellent sectionizing qualities of the Duncan grapefruit with the fresh eating characteristics of the King orange. The juice is easily concentrated and has a distinctive flavor that might best be described as a cross between the flavor of the Duncan grapefruit and that of the King orange.

The accompanying illustration shows two of the fruits of the new variety which have been sliced through the center to illustrate the interior as well as the exterior thereof, together with portions of the stems and leaves.

The following is a detailed description of the new variety, with color plate identifications in accordance with Maerz and Paul, A Dictionary of Color (McGraw Hill—1950).

The tree is of medium size with many of the appearances of the Valencia orange tree (unpatented), although its growth is slightly more erect. The number and size of the thorns approximate those of the King orange.

The leaves of the tree are elliptical and exhibit a pronounced cup. They are dark green in color (22 I 10) with relatively narrow petioles of a length slightly greater than the petioles of the King orange leaf.

As shown in the accompanying illustration, the fruit of the new variety has a rind which has a distinct orange blush (10 K 6), while the flesh of the fruit is deep orange (10 F 9). Other descriptive characteristics of the fruit will be apparent from the following outline:

External surface: Smooth to finely papillate.
Shape: Oblate to globose or slightly obovate.
Size: Large; transverse diameter measuring 4.25 inches to 5.25 inches, average 4.75 inches.
Calyx: Small to medium, depressed.
Rind: Medium thickness, average .188 inch; oil cells medium large.
Sections: Average 10 per fruit, separating readily; rag from rind medium.
Juice: Content abundant; easily concentrated; 1.08 percent acid; 12.85 percent solid; flavor excellent, approximate cross between flavor of King orange and Duncan grapefruit with King slightly predominant.
Seeds: Size, medium large; shape, cuneate or broadly clavate to obovoid; average number, 15 per fruit; evenly spaced, with about one or two seeds per segment.
Season: Late midseason to early late.

The new variety has much the same facility for producing large crops of fruit as the regular Valencia orange. In addition, it has exhibited a marked resistance to cold weather. As an illustration, in the winter of 1958, a tree in accordance with this new variety, grown for experimental purposes in Norfolk loam soil on my property in Lakeland, Polk County, Florida, successfully withstood a temperature of 24 degrees Fahrenheit for 5.5 hours without serious injury. The hardness of the new variety is considerably greater than that of the Valencia orange and approximates the hardiness of many of the trees in the mandarin orange group.

It will be noted from the above description that the new variety substantially resembles the Valencia orange as regards the tree, although it has exhibited considerably greater resistance to cold weather. The fruit of the new variety, on the other hand, approximates the Duncan grapefruit in size, while the color of the flesh resembles that of the King orange. The flavor is excellent and is easily distinguished from the flavor of the Valencia orange and that of each of the parents.

What is claimed is:

A new and distinct variety of tangelo tree substantially as described and illustrated, characterized particularly by the excellent sectionalizing qualities and distinctive color and flavor of the fruit.

No references cited.